United States Patent
Tadros

(10) Patent No.: US 9,861,646 B2
(45) Date of Patent: Jan. 9, 2018

(54) DENTAL COMPOSITIONS

(71) Applicant: Ozdent Pty Ltd, Castle Hill, New South Wales (AU)

(72) Inventor: Joshua George Tadros, Castle Hill (AU)

(73) Assignee: OZDENT PTY LTD, Castle Hill, New South Wales (AU)

( * ) Notice: Subject to any disclaimer, the term of this patent is extended or adjusted under 35 U.S.C. 154(b) by 0 days.

(21) Appl. No.: 14/440,137

(22) PCT Filed: Nov. 1, 2013

(86) PCT No.: PCT/AU2013/001268
§ 371 (c)(1),
(2) Date: May 1, 2015

(87) PCT Pub. No.: WO2014/066951
PCT Pub. Date: May 8, 2014

(65) Prior Publication Data
US 2015/0328236 A1 Nov. 19, 2015

(30) Foreign Application Priority Data
Nov. 2, 2012 (AU) .............................. 2012904856

(51) Int. Cl.
*A61K 31/65* (2006.01)
*A61K 9/00* (2006.01)
*A61K 47/02* (2006.01)
*A61K 47/18* (2017.01)
*A61K 31/58* (2006.01)
*A61K 47/10* (2017.01)
*A61K 6/00* (2006.01)
*A61K 31/573* (2006.01)

(52) U.S. Cl.
CPC ............ *A61K 31/65* (2013.01); *A61K 6/0032* (2013.01); *A61K 6/0041* (2013.01); *A61K 9/0053* (2013.01); *A61K 31/573* (2013.01); *A61K 31/58* (2013.01); *A61K 47/02* (2013.01); *A61K 47/10* (2013.01); *A61K 47/183* (2013.01)

(58) Field of Classification Search
USPC .................................................. 424/49, 401
See application file for complete search history.

(56) References Cited

U.S. PATENT DOCUMENTS

| | | | | |
|---|---|---|---|---|
| 5,624,906 A | * | 4/1997 | Vermeer | ................... A61K 8/60 514/23 |
| 2002/0137728 A1 | * | 9/2002 | Montgomery | ........... A61K 8/02 514/99 |
| 2013/0344120 A1 | * | 12/2013 | Scott | ..................... A61Q 11/00 424/401 |

FOREIGN PATENT DOCUMENTS

| | | |
|---|---|---|
| RU | 2270018 | 2/2006 |
| WO | 8805650 | 8/1988 |
| WO | 9956701 | 11/1999 |

OTHER PUBLICATIONS

Patton et al., "Effects of Doxycycline and Antiinflammatory Agents on Experimentally Induced Chlamydial Upper Genital Tract Infection in Female Macaques." J Infect Dis. (1997) 173(3): 648-654.*
Storehagen et al., "Dentifrices and Mouthwashes Ingredients and their use." Semesteroppgave 10, semester Kull V99, Det odontologiske fakultet, Universitetet i Oslo; 2003.*
Ruiz-Roca et al., "Pyostomatitis vegetans. Report of two cases and review literature." Oral Surg Oral Med Oral Pathol Oral Radiol Endol 2005;99:447-54.*
International Search Report for PCT/AU2013/001268 filed Nov. 1, 2013, Applicant Ozdent Pty Ltd.
Wong et al., The effect of intracanal Ledermix on root resorption of delayed-replanted monkey teeth, Dental Traumatology 2002, 18: 309-315.
Extended European Search Report dated Apr. 21, 2016 for 13850903-1453/2914233 PCT/AU2013001268, Applicant Oxdent Pty Ltd.
Chen et al., Discoloration of Roots Caused by Residual Endodontic Intracanal Medicaments, The Scientific World Journal, vol. 2014, Article ID 404676, 2014, 9 pages.
Chen et al., Root discolouration following short-term application of steroid medicaments containing clindamycin, doxycycline or demeclocycline, Australian Endodontic Journal, vol. 38, 2012, pp. 124-128.

* cited by examiner

*Primary Examiner* — Walter Webb
(74) *Attorney, Agent, or Firm* — Thorpe North & Western

(57) ABSTRACT

A dental composition comprising a therapeutically effective amount of doxycycline hyclate and a therapeutically effective amount of triamcinolone acetonide and use in dental treatment.

46 Claims, No Drawings

DENTAL COMPOSITIONS

The present application is a National Stage of International Application No. PCT/AU2013/001268, filed on Nov. 1, 2013, which claims priority to AU Application No. 2012904856, filed on Nov. 2, 2012, each of which are incorporated herein by reference in its entirety.

TECHNICAL FIELD

The present invention relates to dental compositions and their use in dental treatment of a mammal. In particular, the invention relates to endodontic compositions and their use in root canal therapy and the treatment of periodontal disease.

BACKGROUND OF THE INVENTION

In the field of dentistry, an important and delicate procedure is the cleaning of a diseased root canal to provide a cavity that is free of diseased tissue and antiseptically prepared for further sterile treatment, such as permanent embalming or filling with an inert or restorative material. This procedure is referred to as root canal therapy (RCT).

A root canal system includes the main root canal and many lateral canals that branch off the main canal, accessory canals, interconnections between the main canals, fins and dentinal tubes. Pulp and periapical diseases are, usually caused by bacteria invading and infecting the root canal system. An infected root canal system contains diseased or dead tissue and bacteria which results in inflammation and severe pain. Bacteria can exist in the root canal system itself or within other regions of the tooth structure such as the dentinal tubules, accessory canals apical deltas etc.

In order to eliminate bacteria from the root canal system a combination of mechanical instrumentation and irrigating solutions are used to remove or dissolve organic and/or inorganic debris, to destroy bacteria, to remove the smear layer and to maintain dentine permeability. As noted above, bacteria can exist in all parts of the tooth root many of which are inaccessible to mechanical and chemical endodontic procedures. Antimicrobial irrigants may reach some of the bacteria beyond the canals but they have limited effect as they are typically only used for a short period of time.

After instrumentation and irrigation, a dental material known as an intracanal medicament is placed into the canal until a later dental appointment when the root canal is filled with a permanent material. The rationale for dividing the treatment into different stages is to allow therapeutically active ingredients from the medicament to exert actions against persisting microorganisms in the root canal system. The intracanal medicament may also contain anti-inflammatory agents which are released into the environment of the root and which reduce the severity of inflammatory responses in the soft and hard tissues adjacent to the root. The primary purpose of intracanal medicaments is to eliminate microbes that have survived the chemomechanical preparation. Bacteria can remain because instrumentation has physical limitations, and irrigants have time limitations. Intracanal medicaments serve to supplement the antibacterial effects of chemomechanical procedures and they can predictably disinfect the root canal system, that is the walls of the root canal itself, the adjacent dentine with its tubular structures, the various accessory and lateral canals, voids and communications which are present, and the tissues immediately adjacent to the root from the crown region of the tooth to the end of the root.

Further purposes of such intracanal medicaments include, to render any remaining canal content inert, to dissolve tissue, to act as a barrier against leakage or breakdown of the temporary filing and to control seepage of apical fluids into the root canal system.

It is desirable that the intracanal medicament is long lasting, such that it is effective for days and possibly weeks after application. One such intracanal medicament (Ledermix) contains both an antibiotic (demeclocycline hydrochloride) and a corticosteroid (triamcinolone acetonide) as the active components and these are able to diffuse over a number of weeks in adult teeth.

Demeclocycline is a member of the tetracycline family of bacteriostatic antibiotics which exert actions on protein synthesis by binding to ribosomes. It has been demonstrated that tetracyclines form a strong reversible bond with hard tissues and that they exhibit slow release over extended periods of time. Antibiotics from this family have been found to exhibit antibacterial substantivity for several weeks.

However, one major problem with the presence of the tetracycline antibiotic demeclocycline in such medicaments is that upon exposure to sunlight teeth staining occurs. This is due to the formation of strongly coloured compounds between the dentine of the roots and crown of teeth and the demeclocycline, which then undergo photo-oxidation. This problem limits the application of medicaments containing demeclocycline in clinical dentistry. When tetracycline antibiotics are ingested during childhood and incorporated into forming tooth structure, a similar issue arises with their incorporation and the formation of further compounds, leading to tooth discolouration. The extent of staining which occurs when tetracyclines are ingested in childhood is known to vary according to the type of tetracycline chosen as well as the dose used and duration of exposure. While it appears that some tetracyclines when ingested in childhood may be less likely to stain teeth, there is no published literature available at the present time which indicates that alternative tetracycline agents could be used in medicament pastes to reduce or overcome the known issues with existing pastes based on demeclocycline.

AU2005220230 discloses a paste which contains clindamycin and triamcinolone as the active components, and claims that use of the paste does not cause staining of the tooth enamel. However, an issue with this choice of agents is the inherent or acquired resistance of major endodontic pathogenic enterococcal bacterial such as *Enterococus facecalis*. This bacterial species is very virulent and is generally found in root canal systems where treatment has failed i.e. the roots have developed an abscess, and the periapical area shows persisting inflammation after root canal treatment. Furthermore, clindamycin has little or no anti-inflammatory properties, and has no substantivity.

There has been a long felt need to provide long lasting medicaments which are more effective in eliminating bacteria from the root canal system, are effective in reducing inflammation, relieving pain and do not result in staining of the tooth structure.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

SUMMARY OF THE INVENTION

In results leading up to the present invention the inventors surprisingly found that when formulated as an intracanal medicament, doxycycline exhibits enhanced antibacterial substantivity for a broader range of bacteria, as compared to currently used intracanal medicaments, without causing severe staining of the tooth structure.

In a first aspect of the invention there is provided an endodontic composition comprising a therapeutically effective amount of doxycycline hyclate and a therapeutically effective amount of triamcinolone acetonide.

In one embodiment according to the first aspect, the therapeutically effective amount of doxycycline hyclate in the endodontic composition reduces and/or eliminates bacteria and reduces inflammation. In another embodiment, the therapeutically effective amount of triamcinolone acetonide in the endodontic composition reduces inflammation. It will be understood that in reducing inflammation there may also be an associated reduction in pain.

According to another embodiment of the first aspect of the invention, there is provided an endodontic composition, when used to reduce and/or eliminate bacteria, reduce inflammation and/or relieve pain in a root canal system. In another embodiment, there is provided an endodontic composition when used to reduce and/or eliminate bacteria from 2 to 4 weeks.

In a second aspect of the invention there is provided a method of reducing and/or eliminating bacteria and reducing inflammation in a root canal system, comprising administering a therapeutically acceptable amount of an endodontic composition according to the first aspect to the root canal system.

In a third aspect of the invention there is provided a method of treating a tooth in need of root canal therapy comprising the steps of administering an endodontic composition according to the first aspect to a root canal system of the tooth, such that subsequent exposure of the tooth to sunlight does not cause staining of the tooth.

Accordingly, in a preferred embodiment, the present invention provides an endodontic composition according to the first aspect for use in root canal therapy, which is effective in reducing and/or eliminating the bacteria from the root canal system for an extended period of time after application and/or reducing inflammation and/or not causing staining of tooth structure.

The present invention also provides an endodontic composition according to the first aspect for the treatment of periodontal disease, particularly for the treatment of chronic periodontitis.

In a fourth aspect of the invention there is provided a method of treating diseased periodontal tissue in a mammal comprising the steps of administering an endodontic composition according to the first aspect to the diseased periodontal tissue.

In a fifth aspect there is provided a use of an endodontic composition according to the first aspect for the manufacture of a medicament for reduction and/or elimination of bacteria and reduction of inflammation in a root canal system of a mammal.

In a sixth aspect there is provided a use of an endodontic composition according to the first aspect for the manufacture of a medicament for the treatment of periodontal disease.

DESCRIPTION OF THE PREFERRED EMBODIMENTS OF THE INVENTION

In one embodiment according to the first aspect, the therapeutically effective amount of doxycycline hyclate or its nanoparticle version is in a range of about 2-12% w/w. In other embodiments, the therapeutically effective amount of doxycycline hyclate is in a range of about 2-10% w/w, about 3-10% w/w, about 4-10 w/w, about 5-10% w/w, about 6-10% w/w, about 7-10% w/w, about 8-10% w/w, about 9-10% w/w, about 2-9% w/w. about 3-9% w/w, about 4-9% w/w, about 5-9% w/w, about 6-9% w/w, about 7-9% w/w, about 8-9% w/w, about 2-8% w/w. about 3-8% w/w, about 4-8% w/w, about 5-8% w/w, about 6-8% w/w, about 7-8% w/w, about 2-7% w/w, about 3-7% w/w, about 4-7% w/w, about 5-7% w/w, about 6-7% w/w, about 2-6% w/w, about 3-6% w/w, about 4-6% w/w, about 5-6% w/w, about 2-5% w/w, about 3-5% w/w, about 4-5% w/w, about 2-4% w/w, about 3-4% w/w or about 2-3% w/w. In examples of the first aspect, the therapeutically effective amount of doxycycline hyclate is about 2% w/w, about 3% w/w, about 4% w/w, about 5% w/w, about 6% w/w, about 7% w/w, about 8% w/w, about 9% w/w or about 10% w/w.

In another embodiment according to the first aspect, the therapeutically effective amount of triamcinolone acetonide is from about 0.5-5% w/w. In other embodiments, the therapeutically effective amount of triamcinolone acetonide is in a range of about 0.5-4% w/w, 1-4% w/w, 1.5-4% w/w, 2-4% w/w, 2.5-4% w/w, 3-4% w/w, 3.5-4% w/w, 0.5-3% w/w, about 1-3% w/w, about 1.5-3% w/w, about 2-3% w/w, about 2.5-3% w/w, about 0.5-2% w/w, 1-2% w/w, 1.5-2% w/w, about 0.5-1.5% w/w or about 0.5-1% w/w. In examples of the first embodiments, the therapeutically effective amount of triamcinolone acetonide is about 0.5% w/w, about 1% w/w, about 1.5% w/w, about 2% w/w, about 2.5% w/w, about 3% w/w, about 3.5% w/w, about 4% w/w or about 5% w/w.

According to the first aspect of the invention, the endodontic composition can further comprises at least one pharmaceutically acceptable carrier selected from the group consisting of glycerol; polyalkylene glycol, acids such as oleic acid; water; ethanol; silicone-based materials (both non-volatile and volatile) such as cyclomethicone, dimethicone and dimethiconecopolyol; hydrocarbons such as squalane, squalene and petrolatum, especially squalane and petrolatum; a sustained release vehicle such as a microsponge or a polymer matrix; surfactants, such as cationic and amphoteric surfactants; a stabilising agent; a suspending agent; an emulsifying agent; a pH regulator such as a citrate or a phosphate salt; or a combination thereof. Other vehicles suitable for use with the compositions would also be known from the cosmetic and pharmaceutical arts.

In one embodiment the carrier is a polyalkylene glycol which is in liquid form. The polyalkylene glycols are those recognised as safe for use in medical or food applications. In particular embodiments, the polyalkylene glycol is selected from polyC2-C3alkylene glycols, for example, polyethylene glycol (PEG) and polypropylene glycol (PPG). Polyalkylene glycols are polymeric ethers and therefore come in a variety of different molecular weights. Polyalkylene glycols may have a number that approximately corresponds to their molecular weight. In some embodiments, the polyalkylene glycol solvent has a molecular weight of, 700 or less or a mixture thereof; especially a polyalkylene glycol with a molecular weight of from 100 to 700 or a mixture thereof; or a polyalkylene glycol with a molecular weight of from 200 to 600 or a mixture thereof; more especially a polyalkylene glycol with a molecular weight of from 300 to 500 or a mixture thereof; most especially polyalkylene glycol 400.

The polyalkylene glycol solvent may be selected from PEG 200, PEG 300, PEG 400, PEG 500, PEG 600, PEG 700, PPG 200, PPG 300, PPG 400, PPG 500, PPG 600 and PPG 700 or a combination thereof; for example from PEG 200, PEG 300, PEG 400, PEG 500, PEG 600, PPG 200, PPG 300, PPG 400, PPG 500 and PPG 600 or a combination thereof; or for example from PEG 300, PEG 400, PEG 500, PPG 300, PPG 400 and PPG 500 or a combination thereof; or for example from PEG 400 or PPG 400.

The carrier can be present in a range of about 0-70% w/w, about 10-70% w/w, about 20-70% w/w, about 30-70% w/w, about 40-70% w/w, about 40-70% w/w, about 50-70% w/w, about 60-70% w/w, about 0-60% w/w, about 10-60% w/w, about 20-50% w/w, about 30-60% w/w, about 40-60% w/w, about 50-60% w/w, about 0-50% w/w, about 10-50% w/w, about 20-50% w/w, about 30-50% w/w, about 40-50% w/w, about 0-40% w/w, about 10-40% w/w, about 20-40% w/w, about 30-40% w/w, about 0-30% w/w, about 10-30% w/w, about 20-30% w/w, about 0-20% w/w, about 10-20% w/w, or about 0-10% w/w. In one embodiment, at least one carrier is water in a concentration range of about 0-25% w/w, about 5-25% w/w, about 10-25% w/w, about 15-25% w/w, about 20-25% w/w, about 0-20% w/w, about 5-20% w/w, about 10-20% w/w, about 15-20% w/w, about 0-15% w/w, about 5-15% w/w, about 10-15% w/w, about 0-10% w/w or about 5-10% w/w. In another embodiment the water concentration is in a range of about 0-5% w/w.

In another embodiment according to the first aspect, at least one carrier is PEG 400 in a concentration range of about 20-70% w/w. In a preferred embodiment, the PEG 400 concentration is in a range of about 30-70% w/w. In some examples, the PEG 400 concentration is about 40% w/w, about 41% w/w, about 42% w/w, about 43% w/w, about 44% w/w, about 45% w/w, about 46% w/w, about 47% w/w, about 48% w/w, about 49% w/w or about 50% w/w.

In some embodiments, the medicament composition further comprises at least one viscosity modifier. The viscosity modifier may be a polyalkylene glycol polymer with a molecular weight of at least 1000, for example a polyethylene glycol or polypropylene glycol with a molecular weight of at least 1000. In some embodiments, the viscosity modifier is a PEG or PPG with a molecular weight of from 2300 to 6000 or a mixture thereof; for example a PEG or PPG with a molecular weight of from 2600 to 4000 or a mixture thereof; or a PEG or PPG with a molecular weight of from 2800 to 4000 or a mixture thereof; or a PEG or PPG with a molecular weight of from 3000 to 3750 or a mixture thereof; or for example a PEG or PPG with a molecular weight of from 3250 to 3500 or a mixture thereof; or in another example PEG 3350 or PPG 3350. Exemplary polyalkylene glycol viscosity modifiers include PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PPG 1000, PPG 1200, PPG 2000, PPG 3000 and PPG 4000.

In one embodiment according to the first aspect at least one viscosity modifier is PEG 3350 in a concentration range of about 2-10% w/w, about 3-10% w/w, about 4-10% w/w, about 5-10% w/w, about 6-10% w/w, about 7-10% w/w, about 8-10% w/w, about 9-10% w/w, about 2-9% w/w, about 3-9% w/w, about 4-9% w/w, about 5-9% w/w, about 6-9% w/w, about 7-9% w/w, about 8-9% w/w, about 2-8% w/w, about 3-8% w/w, about 4-8% w/w, about 5-8% w/w, about 6-8% w/w, about 7-8% w/w, about 2-7% w/w, about 3-7% w/w, about 4-7% w/w, about 5-7% w/w, about 6-7% w/w, about 2-6% w/w, about 3-6% w/w, about 4-6% w/w, about 5-6% w/w, about 2-5% w/w, about 3-5% w/w, about 4-5% w/w, about 2-4% w/w or about 3-4% w/w. In some examples, the PEG 3350 concentration is about 2% w/w, about 3% w/w, about 4% w/w, about 5% w/w, about 6% w/w, about 7% w/w, about 8% w/w, about 9% w/w, about 10% w/w.

According to the first aspect of the invention, preferably the endodontic composition further comprises at least one bulking agent. Suitable bulking agents may be selected from one or more of the group consisting of zinc oxide and fumed silica. The total concentration of bulking agent in one embodiment is in a range from about 0-55% w/w. In one embodiment, at least one bulking agent is zinc oxide. In some examples, the zinc oxide is in a concentration range of about 5-50% w/w, about 10-50% w/w, about 20-50% w/w, about 30-50% w/w, about 40-50% w/w, about 5-40% w/w, about 10-40% w/w, about 20-40% w/w, about 30-40% w/w, about 5-30% w/w, about 10-30% w/w, about 20-30% w/w, about 5-20% w/w or about 10-20% w/w. In some further examples, the zinc oxide is in a concentration of about 5% w/w, 6% w/w, 7% w/w, 8% w/w, 9% w/W, 10% w/w, or in a concentration of 25% w/w, about 26% w/w, about 27% w/w, about 28% w/w, about 29% w/w, about 30% w/w, about 31% w/w, about 32% w/w, about 33% w/w, about 34% w/w, or about 35% w/w.

The addition of zinc oxide adds bulk to the composition and contributes towards making the composition white in colour.

In another embodiment, at least one bulking agent is fumed silica such as Aerosil® 200. In one form, the fumed silica concentration is in a range from about 0-2% w/w. In some examples, the fumed silica concentration is about 1% w/w, about 1.5% w/w, or about 2% w/w.

The addition of fumed silica, such as Aerosil® 200, to the composition adds bulk to the carrier vehicle and also improves the free flowing characteristics.

According to the first aspect of the invention, in other embodiments the endodontic composition further comprises at least one drying agent. For example, the drying agents can be present in a range of from, about 0-5% w/w. In some examples, the drying agents are present in an amount of about 1% w/w, about 2% w/w, about 3% w/w, about 4% w/w, or about 5% w/w. Suitable drying agents include but are not limited to calcium chloride. In one embodiment, at least one drying agent is calcium chloride. In some embodiments, the calcium chloride is in a concentration range of about 0-3% w/w. In some examples, the calcium chloride concentration is about 1% w/w, about 2% w/w, or about 3% w/w.

According to the first aspect of the invention, the endodontic composition can further comprise at least one preservative. Suitable preservatives may be selected from one or more of the group consisting of sodium metabisulfite, sodium sulfite, disodium ethylenediaminetetraaceticacid (EDTA), benzoic acid and hydroxyethyl benzoate. In some embodiments, the preservative is present in a concentration range of about 0-3% w/w. In one embodiment, at least one preservative is sodium metabisulfite. In some embodiments, the sodium metabisulfite, concentration is in a range of about 0-3% w/w. In some examples the sodium metabisulfite, concentration is about 0.5% w/w, about 1% w/w, about 1.5%-w/w, about 2% w/w, about 2.5% w/w, or about 3% w/w.

In another embodiment according to the first aspect, at least one preservative is disodium ethylenediaminetetraaceticacid (EDTA). In some examples, the EDTA concentration is in a range from 0-3% w/w. In some embodiments, the EDTA concentration is about 1% w/w, about 2% w/w, or about 3% w/w. The presence of EDTA in the composition also contributes towards neutralizing the composition.

According to the first aspect of the invention, preferably the endodontic composition further comprises at least one base. Suitable bases may be selected from one or more of the group consisting of triethanolamine, sodium hydroxide or sodium hexametaphosphate. The base may be in a concentration range of about 0-5% w/w. In one embodiment, at least one base is triethanolamine. In some embodiments, the triethanolamine concentration range is about 0-3% w/w. In some examples, the triethanolamine concentration is about 1% w/w, about 1.5% w/w, about 2% w/w, about 2.5% w/w, or about 3% w/w.

In addition to its action as a base, the triethanolamine acts as a surfactant and emulsifier.

In yet another embodiment according to the first aspect, the at least one base is sodium hydroxide. In one embodiment, the sodium hydroxide concentration is in a range of about 0-2% w/w. In some examples, the sodium hydroxide concentration is about 0.5% w/w, about 1% w/w, about 1.5% w/w, or about 2% w/w.

According to the first aspect of the invention, the endodontic composition can further comprises at least one white pigment. In some embodiments, the pigment is present in a range of about 0-10% w/w, for example about 3% w/w, about 4% w/w, about 5% w/w, about 6% w/w, about 7% w/w. The white pigment may be selected from the group consisting of titanium dioxide, calcium tungstate, zirconium dioxide, magnesium oxide or barium sulphate. In one embodiment, at least one white pigment is titanium dioxide. In some embodiments, the titanium dioxide concentration is in a range of about 0-6% w/w, or about 0-10% w/w. In some examples, the titanium dioxide concentration is about 3% w/w, about 4% w/w, about 5% w/w, about 6% w/w, about 7% w/w.

According to the first aspect of the invention, the endodontic composition can further comprises at least one antioxidant. Suitable antioxidants may be selected from one or more of the group consisting of butylated hydroxyanisole (BHA), butylated hydroxytoluene (BHT), vitamin C, sodium ascorbate, sodium metabisulfite, sodium sulphite, vitamin E, Coenzyme Q10, e-Viniferin (also known as Grape Reservatrol) Flavoniods (also called Polyphenols), Grape Seed Extract and methyl salicylate. The total concentration of antioxidant in some embodiments is from about 1-10% w/w. For example, the antioxidant concentration is from about 5-8% w/w. In some examples the antioxidant concentration is about 1% w/w, about 2% w/w, about 3% w/w, about 4% w/w, about 5% w/w, about 6% w/w, about 7% w/w, about 8% w/w, about 9% w/w, or about 10% w/w.

In yet another embodiment according to the first aspect of the invention, the endodontic composition may also further comprise a radiopaquing agent. Exemplary radiopaquing agents include strontium, zirconium, lanthanum, tungsten, bismuth or barium compounds; especially zirconium or barium compounds; more especially zirconium compounds. In some embodiments, the radiopaquing agent is selected from strontium oxide, zirconium silicate, zirconium oxide, zirconium dioxide, lanthanum oxide, calcium tungstate, bismuth oxide, barium zirconate and barium sulphate or a combination thereof; more especially zirconium dioxide and barium sulphate; most especially zirconium dioxide. The total concentration of radioplaquing in some embodiments is from about 0-30% w/w; about 0-25% w/w, about 15-25% w/w, about 18% w/w, about 21% w/w.

According to the first aspect of the invention, in some embodiments the endodontic composition is an intracanal medicament.

In yet another embodiment according to the first aspect, the endodontic composition is a paste.

Structural modification of the original natural tetracyclines, such as demeclocycline, led to the development of semi-synthetic derivatives such as doxycycline and minocycline, compounds which possess higher lipophilicity, better oral pharmacokinetics and higher potency. Accordingly, there are a number of advantages of using doxycycline in an intracanal medicament, especially when compared to demeclocycline. Without being bound to any particular theory, doxycycline has a better spectrum of antibiotic activity, especially in relation to *Streptococcus pyogenes*, enterococci and other anerobes. Doxycycline is also more soluble in lipids and exhibits antibacterial substantivity for a longer period of time than demeclocycline. Furthermore, doxycycline has been extensively evaluated in human clinical trials revealing additional therapeutic benefits to its use. In particular, it has been shown that low doses of doxycycline are inhibitors of matrix metalloproteinase enzymes (MMPs). MMPs are among the key mediators of irreversible tissue destruction in periodontitis and peri-implantitis. Doxycycline inhibits MMP, and thus slows down tissue degradation, independently of its desirable antimicrobial properties.

Tetracyclines suppress cytokine levels such as tumor necrosis factor alpha (TNF$\alpha$), interleukin 1 beta (IL-1$\beta$) and interleukin six (IL-6) under pathological conditions and in particular where inflammation is involved. These cytokines are known to play essential roles in the process of inflammation. Thus, antibodies that neutralize the cytokine, their receptors or interfere with their signalling pathways are used in the clinic for the treatment of inflammatory diseases.

Accordingly, another beneficial therapeutic effect of doxycycline is that it reduces cytokine TNF-$\alpha$, IL-6 and IL-1$\beta$ production by human mononuclear inflammatory cells when stimulated by endotoxin (the lipopolysaccharide component of membranes of Gram negative bacteria). Endotoxin induces the production of proinflammatory cytokines, TNF-$\alpha$ and IL-1$\beta$, which can mediate connective tissue breakdown and bone resorption, locally. The local effect is a likely host-mediated pathogenic pathway for microbially induced bone loss in both endodontic infections and in periodontal disease.

Accordingly, in some embodiments of the first, second and fifth aspects of the invention the inflammation is reduced by inhibiting matrix metalloproteinase enzymes in a root canal system. In another embodiment, the inflammation is reduced by effectively reducing cytokine production by human mononuclear inflammatory cells when stimulated by endotoxin, in a root canal system.

In yet another embodiment according to the first, second and fifth aspects of the invention, the inflammation is reduced by inhibiting osteoclasts in a root canal system.

In another embodiment according to the fourth aspect, the diseased periodontal tissue is a periodontal pocket around a tooth or around a dental implant.

In another embodiment of the sixth aspect of the invention, the periodontal disease is chronic periodontitis or peri-implantitis. For example, the chronic periodontitis is treated by the application of an endodontic composition, according to the first aspect, in the form of a paste to the periodontal pocket.

It should be understood that in addition to the ingredients particularly mentioned above, the formulations may include other agents conventional in the art having regard to the type of formulation in question.

The composition of the present invention may be suitable for the dental treatment of a human or animal patient. In one embodiment, the patient is a mammal including a human, horse, dog, cat, sheep, cow, or primate. In one embodiment the patient is a human. In a further embodiment, the patient is not a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "treatment" refers to defending against or inhibiting a symptom, treating a symptom, delaying the appearance of a symptom, reducing the severity of the development of a symptom, and/or reducing the number or type of symptoms suffered by an individual, as compared to not administering a pharmaceutical composition comprising a compound of the invention. The term treatment encompasses the use in a palliative setting.

Throughout this specification the phrase "root canal system" will be understood to mean the area covered by the walls of the root canal itself, the adjacent dentine with its tubular structures, the various accessory and lateral canals, voids and communications which are present, and the tissues immediately adjacent to the root from the crown region of the tooth to the end of the root.

Throughout this specification the phrase "intradental medicament" will be understood to mean a medicament for which the primary objective is to eliminate microbes that have survived the chemomechanical preparation of the root canal system. Accordingly, such medicaments serve to supplement the antibacterial effects of chemomechanical procedures and predictably disinfect the root canal system.

Throughout the specification and as referred to in the third aspect of the invention, reference to the tooth will be understood to mean the tooth structure.

It will be understood that the endodontic composition is usually applied to the empty root canal system. Following the root canal therapy procedure known to those skilled in the art, it will be understood that the endodontic composition will also be present and effective in the treated root canal system following irrigation and filling. Accordingly, "root canal system" will be understood to encompass both the empty and non-empty or treated root canal systems.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

EXAMPLE EMBODIMENTS

A. An endodontic composition comprising a therapeutically effective amount of doxycycline hyclate and a therapeutically effective amount of triamcinolone acetonide.

B. An endodontic composition according to embodiment A, wherein the therapeutically effective amount of doxycycline hyclate is in a range of about 2-12% w/w, about 2-10% w/w, about 3-10% w/w, about 4-10 w/w, about 5-10% w/w, about 6-10% w/w, about 7-10% w/w, about 8-10% w/w, about 9-10% w/w, about 2-9% w/w. about 3-9% w/w, about 4-9% w/w, about 5-9% w/w, about 6-9% w/w, about 7-9% w/w, about 8-9% w/w, about 2-8% w/w. about 3-8% w/w, about 4-8% w/w, about 5-8% w/w, about 6-8% w/w, about 7-8% w/w, about 2-7% w/w, about 3-7% w/w, about 4-7% w/w, about 5-7% w/w, about 6-7% w/w, about 2-6% w/w, about 3-6% w/w, about 4-6% w/w, about 5-6% w/w, about 2-5% w/w, about 3-5% w/w, about 4-5% w/w, about 2-4% w/w, about 3-4% w/w or about 2-3% w/w.

C. An endodontic composition according to embodiment B, wherein the therapeutically effective amount of doxycycline hyclate is in a range of about 2-10% w/w.

D. An endodontic composition according to embodiment C, wherein the therapeutically effective amount of doxycycline hyclate is about 2% w/w, about 3% w/w, about 4% w/w, about 5% w/w, about 6% w/w, about 7% w/w, about 8% w/w, about 9% w/w or about 10% w/w.

E. An endodontic composition according to embodiment A, wherein the therapeutically effective amount of triamcinolone acetonide is in a range of about 0.5-5% w/w, about 0.5-4% w/w, 1-4% w/w, 1.5-4% w/w, 2-4% w/w, 2.5-4% w/w, 3-4% w/w, 3.5-4% w/w, 0.5-3% w/w, about 1-3% w/w, about 1.5-3% w/w, about 2-3% w/w, about 2.5-3% w/w, about 0.5-2% w/w, 1-2% w/w, 1.5-2% w/w, about 0.5-1.5% w/w or about 0.5-1% w/w.

F. An endodontic composition according to embodiment E, wherein the therapeutically effective amount of triamcinolone acetonide is about 0.5% w/w, about 1% w/w, about 1.5% w/w, about 2% w/w, about 2.5% w/w, about 3% w/w, about 3.5% w/w, about 4% w/w or about 5% w/w.

G. An endodontic composition according to embodiment E or F, wherein the therapeutically effective amount of triamcinolone acetonide is in a range of about 1-3% w/w.

H. An endodontic composition according to any one of example embodiments further comprising at least one pharmaceutically acceptable carrier in a concentration range of about 0-70% w/w, about 10-70% w/w, about 20-70% w/w, about 30-70% w/w, about 40-70% w/w, about 40-70% w/w, about 50-70% w/w, about 60-70% w/w, about 0-60% w/w, about 10-60% w/w, about 20-50% w/w, about 30-60% w/w, about 40-60% w/w, about 50-60% w/w, about 0-50% w/w, about 10-50% w/w, about 20-50% w/w, about 30-50% w/w, about 40-50% w/w, about 0-40% w/w, about 10-40% w/w, about 20-40% w/w, about 30-40% w/w, about 0-30% w/w, about 10-30% w/w. about 20-30% w/w, about 0-20% w/w, about 10-20% w/w, or about 0-10% w/w.

I. An endodontic composition according to embodiment H, wherein at least one pharmaceutically acceptable carrier is selected from the group consisting of water, polyC$_2$-C$_3$alkylene glycol.

J. An endodontic composition according to embodiment I, wherein at least one pharmaceutically acceptable carrier is water in a concentration range of about 0-25% w/w, about 5-25% w/w, about 10-25% w/w, about 15-25% w/w, about 20-25% w/w, about 0-20% w/w, about 5-20% w/w, about 10-20% w/w, about 15-20% w/w, about 0-15% w/w, about 5-15% w/w, about 10-15% w/w, about 0-10% w/w or about 5-10% w/w.

K. An endodontic composition according to embodiment J, wherein the water concentration is in a range of about 0-5% w/w.

L. An endodontic composition according to any one of embodiment H to K, wherein at least one pharmaceutically acceptable carrier is a polyethylene glycol with a molecular of about 400.

M. An endodontic composition according to embodiment L, wherein the polyethylene glycol concentration is about 40% w/w, about 41% w/w, about 42% w/w, about 43% w/w, about 44% w/w, about 45% w/w, about 46% w/w, about 47% w/w, about 48% w/w, about 49% w/w or about 50% w/w.

N. An endodontic composition according to any one of the example embodiments, further comprising a viscosity modifier.

O. An endodontic composition according to embodiment N, wherein the viscosity modifier is selected from a polyalkylene glycol polymer with a molecular weight of at least 1000.

P. An endodontic composition according to embodiment O, wherein the polyalkylene glycol is a polyethylene glycol or polypropylene glycol with a molecular weight of from 2300 to 6000.

Q. An endodontic composition according to any one of example embodiments N to P, wherein at least one viscosity modifier is polyethylene glycol with a molecular weight of about 3350 in a concentration range of about 2-10% w/w, about 3-10% w/w, about 4-10% w/w, about 5-10% w/w, about 6-10% w/w, about 7-10% w/w, about 8-10%, w/w, about 9-10% w/w, about 2-9% w/w, about 3-9% w/w, about 4-9% w/w, about 5-9% w/w, about 6-9% w/w, about 7-9% w/w, about 8-9% w/w, about 2-8% w/w, about 3-8% w/w, about 4-8% w/w, about 5-8% w/w, about 6-8% w/w, about 7-8% w/w, about 2-7% w/w, about 3-7% w/w, about 4-7% w/w, about 5-7% w/w, about 6-7% w/w, about 2-6% w/w, about 3-6% w/w, about 4-6% w/w, about 5-6% w/w, about 2-5% w/w, about 3-5% w/w, about 4-5% w/w, about 2-4% w/w or about 3-4% w/w.

R. An endodontic composition according to embodiment Q, wherein the polyethylene glycol concentration is about 2% w/w, about 3% w/w, about 4% w/w, about 5% w/w, about 6% w/w, about 7% w/w, about 8% w/w, about 9% w/w, about 10% w/w.

S. An endodontic composition according to any one of the example embodiments further comprising at least one bulking agent.

T. An endodontic composition according to embodiment S, wherein the at least one bulking agent is in a concentration of about 0-55% w/w.

U. An endodontic composition according to embodiment S, wherein the bulking agent is zinc oxide is in a concentration of about 5-50% w/w.

V. An endodontic composition according to embodiment U, wherein the zinc oxide is in a concentration of about 5% w/w, about 6% w/w, about 7% w/w, about 8% w/w, 9% w/w, about 10% w/w, about 29% w/w, about 25% w/w, about 26% w/w, about 27% w/w, about 28% w/w, about 30% w/w, about 31% w/w, about 32% w/w, about 33% w/w, about 34% w/w, or about 35% w/w.

W. An endodontic composition according to any one of example embodiments S to V, wherein at least one bulking agent is fumed silica.

X. An endodontic composition according to embodiment W, wherein the fumed silica concentration is in a range of about 0-2% w/w, about 1% w/w, about 1.5% w/w, or about 2% w/w.

Y. An endodontic composition according to any one of the example embodiments further comprising at least one drying agent.

Z. An endodontic composition according to embodiment Y, wherein the at least one drying agent is in a range of about 0-5% w/w, about 1% w/w, about 2% w/w, about 3% w/w, about 4% w/w, or about 5% w/w.

AA. An endodontic composition according to embodiment Z, wherein the drying agent is calcium chloride.

AB. An endodontic composition according to embodiment AA, wherein the calcium chloride concentration is in a range of about 0-3% w/w.

AC. An endodontic composition according to embodiment AB, wherein the calcium chloride concentration is about 2% w/w, about 1% w/w, or about 3% w/w.

AD. An endodontic composition according to any one of the example embodiments further comprising at least one preservative.

AE. An endodontic composition according to embodiment AD, wherein at least one preservative is in a concentration in a range of about 0-3% w/w, or about 0.5% w/w, about 1% w/w, about 1.5% w/w, about 2% w/w, about 2.5% w/w, or about 3% w/w.

AF. An endodontic composition according to embodiments AD or AE, wherein the preservative is sodium metabisulfite.

AG. An endodontic composition according to embodiment AF, wherein the sodium metabisulfite concentration is about 0.5% w/w, about 1% w/w, about 1.5% w/w, about 2% w/w, about 2.5% w/w, or about 3% w/w.

AH. An endodontic composition according to any one of embodiment AD to AE, wherein the at least one preservative is disodium ethylenediaminetetraaceticacid (EDTA).

AI. An endodontic composition according to embodiment AH, wherein the EDTA concentration is in a range of about 1-3% w/w, or about 1% w/w, about 2% w/w, or about 3% w/w.

AJ. An endodontic composition according to any one of the example embodiments, further comprising at least one base.

AK. An endodontic composition according to embodiment AJ, wherein at least one base is triethanolamine.

AL. An endodontic composition according to embodiment AK, wherein the triethanolamine concentration is in a range of about 0-3% w/w.

AM. An endodontic composition according to embodiment AL, wherein the triethanolamine concentration is about 1.5% w/w, about 1% w/w, about 1.5% w/w, about 2% w/w, about 2.5% w/w, or about 3% w/w.

AN. An endodontic composition according to any one of embodiments AJ to AL, wherein at least one base is sodium hydroxide.

AO. An endodontic composition according to embodiment AN, wherein the sodium hydroxide concentration is in a range of about 0-2% w/w, about 0.5% w/w, about 1% w/w, about 1.5% w/w, or about 2% w/w.

AP. An endodontic composition according to any one of the example embodiments, further comprising at least one white pigment.

AQ. An endodontic composition according to embodiment AP, wherein the white pigment is titanium dioxide.

AR. An endodontic composition according to embodiment AQ, wherein the titanium dioxide concentration is in range of about 0-10% w/w or about 0-6%

AS. An endodontic composition according to embodiment AQ, wherein the titanium dioxide concentration is about 5% w/w, about 3% w/w, about 4% w/w, about 6% w/w, about 7% w/w.

AT. An endodontic composition according to any one of the example embodiments, further comprising at least one antioxidant.

AU. An endodontic composition according to embodiment AT, wherein the antioxidant is selected from the group consisting of butylated hydroxyanisole (BHA), butylated hydroxytoluene (BHT), Coenzyme Q10, e-Viniferin, Flavoniods, Grape Seed Extract, sodium sulphite, sodium metabisulfite, vitamin C, sodium ascorbate, vitamin E and methyl salicylate or mixtures thereof, in a total concentration in a range of about 1-10% w/w, about 1% w/w, about 2% w/w, about 3% w/w, about 4% w/w, about 5% w/w, about 6% w/w, about 7% w/w, about 8% w/w, about 9% w/w, or about 10% w/w.

AV. An endodontic composition according to embodiment AU, wherein the antioxidant concentration is in a range of about 5-8%.

AW. An endodontic composition according to any one of the example embodiments comprising at least one radiopaquing agent.

AX. An endodontic composition according to embodiment AW, wherein the radiopaquing agent is a strontium, zirconium, lanthanum, tungsten, bismuth or barium compound, or a mixture thereof.

AY. An endodontic composition according to embodiment AX, wherein the radiopaquing agent is selected from the group consisting of strontium oxide, zirconium silicate, zirconium oxide, zirconium dioxide, lanthanum oxide, calcium tungstate, bismuth oxide, barium zirconate and barium sulphate or a mixture thereof.

AZ. An endodontic composition according to embodiment AY, wherein the radiopaquing agent is zirconium dioxide.

BA. An endodontic composition according to any one of the example embodiments, wherein the composition is an intracanal medicament.

BB. An endodontic composition according to any one of the example embodiments, wherein the composition is a paste.

BC. An endodontic composition according to any one of the example embodiments, wherein the therapeutically effective amount of doxycycline hyclate reduces and/or eliminates bacteria and reduces inflammation.

BD. An endodontic composition according to any one of the example embodiments, wherein the therapeutically effective amount of triamcinolone acetonide reduces inflammation.

BE. An endodontic composition according to any one of the example embodiments, when used to reduce and/or eliminate bacteria and reduce inflammation in a root canal system.

BF. An endodontic composition according to embodiment BE, when used to reduce and/or eliminate bacteria for a period of 2-4 weeks in a root canal system.

BG. An endodontic composition according to embodiments BC or BE, wherein the inflammation is reduced by inhibiting matrix metalloproteinase enzymes.

BH. An endodontic composition according to embodiments BC or BE, wherein the inflammation is reduced by effectively reducing cytokine production by human mononuclear inflammatory cells when stimulated by endotoxin.

BI. An endodontic composition according to embodiments BC or BE, wherein the inflammation is reduced by inhibiting osteoclasts in the root canal system.

BJ. A method of reducing and/or eliminating bacteria and reducing inflammation in a root canal system, comprising administering a therapeutically acceptable amount of an endodontic composition according to any one of embodiments A to BI to the root canal system.

BK. A method according to embodiment BJ, wherein the inflammation is reduced by inhibiting matrix metalloproteinase enzymes.

BL. A method according to embodiment BJ, wherein the inflammation is reduced by effectively reducing cytokine production by human mononuclear inflammatory cells when stimulated by endotoxin.

BM. A method according to embodiment BJ, wherein the inflammation is reduced by inhibiting osteoclasts in the root canal system.

BN. A method of treating a tooth in need of root canal therapy comprising the steps of administering an endodontic composition according to any one of embodiments A to BI to a root canal system of the tooth, such that subsequent exposure of the tooth to sunlight does not cause staining of the tooth.

BO. A method of treating diseased periodontal tissue in a mammal comprising the steps of administering an endodontic composition according to any one of embodiments A to BI to the diseased periodontal tissue.

BP. A method according to embodiment BO, wherein the diseased periodontal tissue is a periodontal pocket around a tooth or around a dental implant.

BQ. Use of an endodontic composition according to any one of embodiments A to BI for the manufacture of a medicament for reduction and/or elimination of bacteria and reduction of inflammation in a root canal system of a mammal.

BR. Use according to embodiment BQ, wherein the reduction of inflammation occurs by inhibiting matrix metalloproteinase enzymes in a root canal system.

BS. Use according to embodiment BQ, wherein the reduction of inflammation occurs by effectively reducing cytokine production by human mononuclear inflammatory cells when stimulated by endotoxin in a root canal system.

BT. Use according to embodiment BQ, wherein the reduction of inflammation occurs by inhibiting osteoclasts in a root canal system.

BU. Use of an endodontic composition according to any one of embodiments A to BI for the manufacture of a medicament for the treatment of periodontal disease.

BV. Use according to embodiment BU, wherein the periodontal disease is chronic periodontitis or peri-implantitis.

MODES FOR CARRYING OUT THE INVENTION

After instrumentation and irrigation, the intracanal medicament is placed into the canal until a later dental appointment when the root canal is filled with a permanent material. The rationale for dividing the treatment into different stages is to allow therapeutically active ingredients from the medicament to exert actions against persisting microorganisms in the root canal system. The anti-inflammatory agents in the medicament are released into the environment of the root and reduce the severity of inflammatory responses in the soft and hard tissues adjacent to the root.

In order to better understand the nature of the invention a endodontic composition of the present invention may be formulated as follows:

Example 1

| Ingredients | Supplier | Percentage (w/w) |
| --- | --- | --- |
| Doxycycline hyclate | Sigma-Aldrich | 8% |
| Triamcinolone acetonide | Sigma-Aldrich | 1% |
| PEG 400 | Sigma-Aldrich | 47% |
| PEG 3350 | Sigma-Aldrich | 5% |
| Zinc oxide (ZnO) | Sigma-Aldrich | 29% |
| Calcium chloride (CaCl) | Sigma-Aldrich | 2% |

-continued

| Ingredients | Supplier | Percentage (w/w) |
| --- | --- | --- |
| Sodium metabisulfite ($Na_2S_2O_5$) | Sigma-Aldrich | 0.5% |
| Disodium ethylenediaminetetraacetic acid (EDTA) | Sigma-Aldrich | 1% |
| Triethanolamine | Sigma-Aldrich | 1.5% |
| Titanium dioxide | Sigma-Aldrich | 5% |

Example 2

| Ingredients | Supplier | Percentage (w/w) |
| --- | --- | --- |
| Doxycycline hyclate | Sigma-Aldrich | 6% |
| Triamcinolone acetonide | Sigma-Aldrich | 1% |
| PEG 400 | Sigma-Aldrich | 48% |
| PEG 3350 | Sigma-Aldrich | 5% |
| Zinc oxide (ZnO) | Sigma-Aldrich | 30% |
| Calcium chloride (CaCl) | Sigma-Aldrich | 2% |
| Sodium metabisulfite ($Na_2S_2O_5$) | Sigma-Aldrich | 0.5% |
| Disodium ethylenediaminetetraacetic acid (EDTA) | Sigma-Aldrich | 1% |
| Triethanolamine | Sigma-Aldrich | 1.5% |
| Titanium dioxide | Sigma-Aldrich | 5% |

Example 3

| Ingredients | Supplier | Percentage (w/w) |
| --- | --- | --- |
| Doxycycline hyclate | Sigma-Aldrich | 3% |
| Triamcinolone acetonide | Sigma-Aldrich | 1% |
| PEG 400 | Sigma-Aldrich | 63.5% |
| PEG 3350 | Sigma-Aldrich | 5% |
| Zinc oxide (ZnO) | Sigma-Aldrich | 16% |
| Calcium chloride (CaCl) | Sigma-Aldrich | 2.0% |
| Sodium metabisulfite ($Na_2S_2O_5$) | Sigma-Aldrich | 1.5% |
| Disodium ethylenediaminetetraacetic acid (EDTA) | Sigma-Aldrich | 1.0% |
| Triethanolamine | Sigma-Aldrich | 2.0% |
| Titanium dioxide | Sigma-Aldrich | 5% |

Example 4

Utilizing Different Antioxidants

| Ingredients | Supplier | Percentage (w/w) |
| --- | --- | --- |
| Doxycycline hyclate | Sigma-Aldrich | 3.0% |
| Triamcinolone acetonide | Sigma-Aldrich | 1.0% |
| PEG 400 | Sigma-Aldrich | 46% |
| PEG 4000 | Sigma-Aldrich | 7.0% |
| Zinc oxide (ZnO) | Sigma-Aldrich | 9.5% |
| butylated hydroxyanisole (BHA) | Sigma-Aldrich | 2.1% |
| Sodium metabisulfite ($Na_2S_2O_5$) | Sigma-Aldrich | 1.0% |
| butylated hydroxytoluene (BHT) | Sigma-Aldrich | 2.1% |
| Silica | Sigma-Aldrich | 1.5 |
| Titanium dioxide | Sigma-Aldrich | 5.0% |
| Zirconium dioxide (ZirO) | Sigma-Aldrich | 21.3% |

Example 5 Utilizing Vitamin C as Antioxidant

| Ingredients | Supplier | Percentage (w/w) |
| --- | --- | --- |
| Doxycycline hyclate | Sigma-Aldrich | 3% |
| Triamcinolone acetonide | Sigma-Aldrich | 1% |
| PEG 400 | Sigma-Aldrich | 45% |
| PEG 4000 | Sigma-Aldrich | 7.0% |
| Zinc oxide (ZnO) | Sigma-Aldrich | 11.0% |
| Calcium chloride (CaCl) | Sigma-Aldrich | 1.0% |
| Sodium metabisulfite ($Na_2S_2O_5$) | Sigma-Aldrich | 3.0% |
| Silica | Sigma-Aldrich | 2.0% |
| Triethanolamine | Sigma-Aldrich | 3.0% |
| Titanium dioxide | Sigma-Aldrich | 4.0% |
| Zirconium dioxide | Sigma-Aldrich | 18.0% |
| vitamin C | Sigma-Aldrich | 2.0% |

Example 1-5 were prepared as follows:

PEG 400 liquid and PEG 3350/4000 are combined in a stainless steel bowl, and the resultant mixture is heated at 50 to 70° C. with constant stirring until the PEG 3350/4000 has melted and dissolved evenly into the mixture, a period of approximately 2 to 3 minutes.

The mixture was then removed from the heat, and the remaining components were added with gentle stirring. The mixture was cooled and mechanically stirred for a period of 5 minutes, and then the mixture was dispensed into tubes and/or syringes.

For Examples 1-3 the following remaining components were sequentially added to the PEG mixture:
(i) doxycycline hyclate;
(ii) triamcinolone acetonide;
iii) sodium metabisulfite
(iv) calcium chloride;
(v) triethanolamine;
(vi) titanium dioxide;
(vii) disodium EDTA; and
(viii) zinc oxide.

Example 4 includes butylated hydroxyanisole (BHA), butylated hydroxytoluene (BHT), sodium metabisulfite as antioxidants and zirconium dioxide as a radiopaquing agent.

For Example 4 the following remaining components were sequentially added to the PEG mixture:
(i) doxycycline hyclate;
(ii) triamcinolone acetonide;
(iii) BHA;
(iv) titanium dioxide;
(v) BHT;
(vi) sodium metasulfate
(vii) zinc oxide,
(viii) titanium dioxide, and
(ix) zirconium dioxide.

Example 5 includes antioxidants and preservatives in the form of Vitamin C and sodium metabisulfite and zirconium dioxide as a radiopaquing agent.

For Example 5 the following remaining components were sequentially added to the PEG mixture: as above for comment in line 10
(i) doxycycline hyclate;
(ii) triamcinolone acetonide;
(iii) calcium chloride;
(iv) triethanolamine;
(v) titanium dioxide;
(vi) silica
(vii) sodium metasulfate
(viii) vitamin C (ix) Zinc oxide, and
(x) zirconium dioxide.

In above Examples 1-5, although sequential order was found not to be important, the inactives were generally added first followed by the actives doxycycline hyclate and triamcinolone acetonide.

Example 6

The formulation was prepared as for examples 1-5 with the addition of 0-10% w/w of water.

Example 7

The formulation was prepared as for example 4 with the addition of 0-2% w/w of sodium hydroxide to adjust the pH within a range of 7.0-7.2.

Example 8

The formulation was prepared as for example 1 and 2 with the addition of 0-2% w/w silicon dioxide (Aerosil® 200).

Example 9

The formulation was prepared as for example 6 with the addition of 5% sodium ascorbate.

Tooth Discolouration Comparative Study

A laboratory study was conducted which compared the extent of tooth discolouration caused by three antibiotic pastes under zero light conditions over 2 and 4 weeks.

The three antibiotic pastes being compared were:

1) a formulation according to Example 3 of the present disclosure containing the tetracycline antibiotic doxycycline and the corticosteroid triamcinolone acetonide.

2) Ledermix paste (Lederle Pharmaceuticals, Wolfrathausen, Germany) containing the tetracycline antibiotic demeclocycline and the corticosteroid triamcinolone, and 3) Odontopaste (Australian Dental Manufacturing, Brisbane, Australia) containing the antibiotic clindamycin and the corticosteroid triamcinolone.

Chemical analysis of the reaction of tetracyclines with tooth structure has revealed that tetracyclines are readily absorbed onto hydroxyapatite mineral, and the bound chelation product then undergoes photo-oxidation which causes light induced staining seen clinically. Past research using the Ledermix paste has shown that most of the demoxycycline in the canal underwent photo-oxidation between 2 and 4 weeks.

The present study evaluates the degree of root discolouration caused by the three antibiotic preparations under zero light conditions over 2 and 4 weeks.

Method

Pilot Study of Material Discolouration

To gauge the effect of light on the materials each of the 3 antibiotic pastes were photographed before and following exposure to visible light (35 Watt xenon high-intensity discharge spotlight). The samples were placed under the lamp and photographed before exposure to visible light source and then after exposure times of 15 min and 45 min.

Discolouration of Roots

Extracted human teeth with closed apices, and no signs of discolouration, previous endodontic treatment, fractures, or restorations were collected and placed in 1% NaOCl for 20 min to degrade external soft tissue remains and the external root was debrided. The crowns were removed to give roots of equal length. The outer root surfaces were polished to improve the quality of image recording. The root canals were prepared to a length of 1 mm short of the apex filed under constant irrigation with alternating 1% NaOCl and 15% ethylene diaminetetraacetic acid (EDTAC) solutions. The canals were dried and stored until placement of the medicament. The roots were photographed and put into labelled vials.

Placement of Medicaments

Medicaments were injected as far apically into the canal as possible under subdued light conditions within less than 30 seconds per root until excess medicament protruded from the apical foramen. The changes in root colour were tracked from baseline in the individual samples using a longitudinal study design where each baseline image acted as the control.

After loading each canal with the relevant paste, each root was placed in a lightproof box and incubated at 100% humidity and at 37° C. to replicate the oral environment in complete darkness.

Data Collection

Each root was photographed to allow standardised views of both sides in a longitudinal view. Each photographical image included a colour reference chip beside the sample to standardise the saturation and brightness of the images. Image analysis was undertaken, measuring the luminosity values of the tooth and the reference chip. From the histogram data the luminosity mean value of the tooth and its colour chip was recorded.

Results

Pilot Study

The colour of the samples from 1) the baseline (before exposure), ii) 15 min exposure and iii) 45 min exposure were compared for each of the antibiotic medicament pastes.

Discolouration of medicament pastes occurred to a marked degree in Ledermix paste from 15 min onwards, with the paste becoming dark brown in colour. Slight darkening of Example 3 of the present invention occurred in the first 15 min which did not progress. No changes were seen in Odontopaste which remained white.

Root Discolouration

The luminosity results are shown in Table 1 below. A lower luminosity value indicates that the root is darker than the baseline situation. Data shows means from 20 teeth (40 data points per group).

| Luminoscity | Odontopaste (OD) | Example 3 (Ex3) | Ledermix (Led) |
|---|---|---|---|
| 2 weeks | 0.98 | 0.96 | 0.88 |
| 4 weeks | 0.97* | 0.94$^{ns}$ | 0.88$^{ns}$ |

Significant values are shown as *$P < 0.05$; $P < 0.001$; *$P < 0.0001$; ns, not significant.

Comparison of luminosity of different pastes:
OD (2 weeks) to Led (2 weeks)—***
OD (2 weeks) to Ex 3 (2 weeks)—ns
OD (4 weeks) to Led (4 weeks)—***
OD (4 weeks) to Ex 3 (4 weeks)—*
Ex3 (2 weeks) to Led (2 weeks)—***
Ex3 (4 weeks) to Led (4 weeks)—***

All samples showed a reduced standardised luminosity over time indicating darkening versus the baseline situation for the same root. The greatest darkening occurred with Ledermix, and least with Odontopaste. Both Odontopaste and Example 3 of the present invention showed slight but progressive darkening of roots between weeks 2 and 4, whereas Ledermix caused marked darkening of roots within 2 weeks but this did not worsen over the subsequent two weeks. Luminosity of roots treated with Ledermix paste was significantly lower at both time intervals compared with Odontapaste and Example 3 of the present invention (p<0.0001). While there was a trend for Example 3 treated roots to be darker than Odontapaste treated roots at both time periods, this did not reach statistical significance at 2 weeks, however at 4 weeks the difference was significant (p<0.05)

The results show that although light can effect certain antibiotic pastes, the reactions which cause discolouration of roots can occur in the absence of exposure to light.

The results of the study show the effects of intense light on Ledermix paste, with marked discolouration of the paste occurring after 15 minutes exposure. It also shows the effect of no light on roots treated with Ledermix (not exposed to light) with significant discolouration occurring after 2 weeks. To minimise the possibility of discolouration, alternative pastes to Ledermix should be considered when teeth in the aesthetic anterior regions of the mouth are treated. Odontopaste and Example 3 of the present invention are alternative non-staining pastes that may be used.

CONCLUSION

This study shows that under zero light conditions staining with Ledermix, a demeclocycline based intra-canal medicament, can still occur. In contrast, Example 3 of the present invention, a doxycycline-based intracanal medicament, caused significantly less staining than Ledermix despite also being a tetracycline based medicament. Clindamycin based intra-canal medicaments do not have any significant effect on staining.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An endodontic composition comprising therapeutically active ingredients consisting essentially of a therapeutically effective amount of doxycycline hyclate and from 0.5-5% w/w of triamcinolone acetonide,
   wherein the therapeutically active ingredients are formulated into the endodontic composition.

2. An endodontic composition according to claim 1, wherein the therapeutically effective amount of doxycycline hyclate is in a range of about 2-12% w/w, about 2-10% w/w, about 3-10% w/w, about 4-10% w/w, about 5-10% w/w, about 6-10% w/w, about 7-10% w/w, about 8-10% w/w, about 9-10% w/w, about 2-9% w/w, about 3-9% w/w, about 4-9% w/w, about 5-9% w/w, about 6-9% w/w, about 7-9% w/w, about 8-9% w/w, about 2-8% w/w, about 3-8% w/w, about 4-8% w/w, about 5-8% w/w, about 6-8% w/w, about 7-8% w/w, about 2-7% w/w, about 3-7% w/w, about 4-7% w/w, about 5-7% w/w, about 6-7% w/w, about 2-6% w/w, about 3-6% w/w, about 4-6% w/w, about 5-6% w/w, about 2-5% w/w, about 3-5% w/w, about 4-5% w/w, about 2-4% w/w, about 3-4% w/w or about 2-3% w/w.

3. An endodontic composition according to claim 1 further comprising at least one pharmaceutically acceptable carrier in a concentration range of about 0-70% w/w, about 10-70% w/w, about 20-70% w/w, about 30-70% w/w, about 40-70% w/w, about 50-70% w/w, about 60-70% w/w, about 0-60% w/w, about 10-60% w/w, about 20-50% w/w, about 30-60% w/w, about 40-60% w/w, about 50-60% w/w, about 0-50% w/w, about 10-50% w/w, about 20-50% w/w, about 30-50% w/w, about 40-50% w/w, about 0-40% w/w, about 10-40% w/w, about 20-40% w/w, about 30-40% w/w, about 0-30% w/w, about 10-30% w/w, about 20-30% w/w, about 0-20% w/w, about 10-20% w/w, or about 0-10% w/w, 0-25% w/w, about 5-25% w/w, about 10-25% w/w, about 15-25% w/w, about 20-25% w/w, about 0-20% w/w, about 5-20% w/w, about 10-20% w/w, about 15-20% w/w, about 0-15% w/w, about 5-15% w/w, about 10-15% w/w, about 0-10% w/w, about 5-10% w/w, or about 0-5% w/w.

4. An endodontic composition according to claim 3, wherein at least one pharmaceutically acceptable carrier is selected from the group consisting of glycerol, polyalkylene glycol, oleic acid, water, ethanol, cyclomethicone, dimethicone, dimethiconecopolyol, squalene, petrolatum, and combinations thereof.

5. An endodontic composition according to claim 3, wherein at least one pharmaceutically acceptable carrier is a polyethylene glycol with a molecular of about 400.

6. An endodontic composition according to claim 1, further comprising a viscosity modifier.

7. An endodontic composition according to claim 6, wherein the viscosity modifier is selected from a polyalkylene glycol polymer with a molecular weight of at least 1000.

8. An endodontic composition according to claim 7, wherein the polyalkylene glycol is a polyethylene glycol or polypropylene glycol with a molecular weight of from 2300 to 6000.

9. An endodontic composition according to claim 1, wherein at least one viscosity modifier is polyethylene glycol with a molecular weight of about 3350 in a concentration range of about 2-10% w/w, about 3-10% w/w, about 4-10% w/w, about 5-10% w/w, about 6-10% w/w, about 7-10% w/w, about 8-10% w/w, about 9-10% w/w, about 2-9% w/w, about 3-9% w/w, about 4-9% w/w, about 5-9% w/w, about 6-9% w/w, about 7-9% w/w, about 8-9% w/w, about 2-8% w/w, about 3-8% w/w, about 4-8% w/w, about 5-8% w/w, about 6-8% w/w, about 7-8% w/w, about 2-7% w/w, about 3-7% w/w, about 4-7% w/w, about 5-7% w/w, about 6-7% w/w, about 2-6% w/w, about 3-6% w/w, about 4-6% w/w, about 5-6% w/w, about 2-5% w/w, about 3-5% w/w, about 4-5% w/w, about 2-4% w/w or about 3-4% w/w.

10. An endodontic composition according to claim 1, further comprising at least one bulking agent.

11. An endodontic composition according to claim 10, wherein the at least one bulking agent is in a concentration of about 0-55% w/w, about 5-50% w/w, about 5% w/w, about 6% w/w, about 7% w/w, about 8% w/w, about 9% w/w, about 10% w/w, about 29% w/w, about 25% w/w, about 26% w/w, about 27% w/w, about 28% w/w, about 30% w/w, about 31% w/w, about 32% w/w, about 33% w/w, about 34% w/w, about 35% w/w, about 0-2% w/w, about 1% w/w, about 1.5% w/w, or about 2% w/w.

12. An endodontic composition according to claim 10, wherein the bulking agent is selected from the group consisting of zinc oxide and fumed silica.

13. An endodontic composition according to claim 1, further comprising at least one drying agent.

14. An endodontic composition according to claim 13, wherein the at least one drying agent is in a range of about 0-5% w/w, about 0-3% w/w, about 1% w/w, about 2% w/w, about 3% w/w, about 4% w/w, or about 5% w/w.

15. An endodontic composition according to claim 14, wherein the drying agent is calcium chloride.

16. An endodontic composition according to claim 1, further comprising at least one preservative.

17. An endodontic composition according to claim 16, wherein at least one preservative is in a concentration in a range of about 0-3% w/w, about 0.5% w/w, about 1% to 3% w/w, about 1% w/w, about 1.5% w/w, about 2% w/w, about 2.5% w/w, or about 3% w/w.

18. An endodontic composition according to claim 16 or 17, wherein the preservative is sodium metabisulfite, sodium sulphite, disodium ethylenediaminetetraacetic acid (EDTA), benzoic acid, hydroxyethyl benzoate, or mixture thereof.

19. An endodontic composition according to claim 16 or 17, wherein the at least one preservative is disodium ethylenediaminetetraaceticacid (EDTA).

20. An endodontic composition according to claim 19, wherein the EDTA concentration is in a range of about 1-3% w/w, or about 1% w/w, about 2% w/w, or about 3% w/w.

21. An endodontic composition according to claim 1, further comprising at least one base.

22. An endodontic composition according to claim 21, wherein the base is selected from the group consisting of triethanolamine, sodium hydroxide, sodium hexametaphosphate, and mixtures thereof.

23. An endodontic composition according to claim 22, wherein the triethanolamine concentration is about 0-3% w/w, about 0-2% w/w, about 0.5% w/w, about 1% w/w, about 1.5% w/w, about 2% w/w, about 2.5% w/w, or about 3% w/w.

24. An endodontic composition according to claim 1, further comprising at least one white pigment.

25. An endodontic composition according to claim 24, wherein the white pigment is titanium dioxide.

26. An endodontic composition according to claim 25, wherein the titanium dioxide concentration is about 0-10% w/w, about 0-6% w/w, about 5% w/w, about 3% w/w, about 4% w/w, about 6%, w/w, or about 7% w/w.

27. An endodontic composition according to claim 1, further comprising at least one antioxidant.

28. An endodontic composition according to claim 27, wherein the antioxidant is one or more of butylated hydroxyanisole (BHA), butylated hydroxytoluene (BHT), Coenzyme-Q10, e-Viniferin, Flavoniods, Grape Seed Extract, sodium sulphite, sodium metabisulfite, vitamin C, sodium ascorbate, vitamin E, or methyl salicylate, in a total concentration in a range of about 1-10% w/w, about 5-8% w/w, about 1% w/w, about 2% w/w, about 3% w/w, about 4% w/w, about 5% w/w, about 6% w/w, about 7% w/w, about 8% w/w, about 9% w/w, or about 10% w/w.

29. An endodontic composition according to claim 1, further comprising at least one radiopaquing agent.

30. An endodontic composition according to claim 29, wherein the radiopaquing agent is a strontium, zirconium, lanthanum, tungsten, bismuth compound, barium compound, or a mixture thereof.

31. An endodontic composition according to claim 30, wherein the radiopaquing agent is presented in an amount ranging from about 0-30% w/w, about 0-25% w/w, or about 15-25% w/w and is selected from the group consisting of strontium oxide, zirconium silicate, zirconium oxide, zirconium dioxide, lanthanum oxide, calcium tungstate, bismuth oxide, barium zirconate, barium sulphate, and a mixture thereof.

32. An endodontic composition according to claim 1, wherein the composition is an intracanal medicament.

33. An endodontic composition according to claim 1, wherein the composition is a paste.

34. An endodontic composition according to claim 1, wherein the therapeutically effective amount of doxycycline hyclate reduces and/or eliminates bacteria and reduces inflammation.

35. An endodontic composition according to claim 1, wherein the therapeutically effective amount of triamcinolone acetonide reduces inflammation.

36. An endodontic composition according to claim 1, when used to reduce and/or eliminate bacteria and reduce inflammation in a root canal system.

37. A method of reducing and/or eliminating bacteria and reducing inflammation in a root canal system, comprising administering a therapeutically acceptable amount of an endodontic composition according to claim 1 to the root canal system.

38. A method of treating a tooth in need of root canal therapy comprising the steps of administering an endodontic composition according to claim 1 to a root canal system of the tooth, such that subsequent exposure of the tooth to sunlight does not cause staining of the tooth.

39. A method of treating diseased periodontal tissue in a mammal comprising the steps of administering an endodontic composition according to claim 1 to the diseased periodontal tissue.

40. An endodontic composition, comprising:
a therapeutically active agent essentially of a therapeutically effective amount of doxycycline hyclate in an amount of about 2-12% w/w a therapeutically effective amount of triamcinolone acetonide in an amount of about 0.5-5% w/w;
one or more pharmaceutically acceptable carriers in an amount of 10-70% w/w selected from the group consisting of glycerol, polyalkylene glycol, oleic acid, water, ethanol, cyclomethicone, dimethicone, dimethiconecopolyol, squalene, and squalene and petrolatum;
at least one viscosity modifier selected from polyalkylene glycol polymers with a molecular weight of at least 1000;
at least one bulking agents in a concentration of about 5-50% w/w selected from the group consisting of zinc oxide and fumed silica;
one or more drying agent in an amount of 0-5% w/w;
at least one preservative in a concentration in a range of about 1-3% w/w selected from one or more of the group consisting of sodium metabisulfite, sodium sulphite, disodium ethylenediaminetetraacetic acid (EDTA), benzoic acid, and hydroxyethyl benzoate;
one or more bases in an amount of from about 0-3% w/w selected from one or more of the group consisting of triethanolamine, sodium hydroxide, and sodium hexametaphosphate;
one or more white pigments in an amount of about 0-10% w/w;
one or more antioxidants in a total concentration range of about 1-10% w/w selected from one or more of the group consisting of butylated hydroxyanisole (BHA), butylated hydroxytoluene (BHT), Coenzyme Q10, e-Viniferin, Flavoniods, Grape Seed Extract, sodium sulphite, sodium metabisulfite, vitamin C, sodium ascorbate, vitamin E, methyl salicylate, or mixtures thereof; and
one or more radiopaquing agents in an amount of about 0-30% w/w selected from the group consisting of strontium oxide, zirconium silicate, zirconium oxide, zirconium dioxide, lanthanum oxide, calcium tungstate, bismuth oxide, barium zirconate, barium sulphate, or mixtures thereof.

41. An endodontic composition according to claim 40, wherein the composition is an intracanal medicament.

42. An endodontic composition according to claim 40, wherein the composition is a paste.

43. An endodontic composition according to claim 40, wherein the therapeutically effective amount of doxycycline hyclate reduces and/or eliminates bacteria and reduces inflammation.

44. An endodontic composition according to claim 40, wherein the therapeutically effective amount of triamcinolone acetonide reduces inflammation.

45. An endodontic composition according to claim 40, when used to reduce and/or eliminate bacteria and reduce inflammation in a root canal system.

46. An endodontic composition according to claim 1, wherein the therapeutically active ingredients consisting of the therapeutically effective amount of doxycycline hyclate and the therapeutically effective amount of triamcinolone acetonide.

* * * * *